US011724010B2

(12) United States Patent
Pomrink et al.

(10) Patent No.: US 11,724,010 B2
(45) Date of Patent: *Aug. 15, 2023

(54) ADHERENT RESORBABLE MATRIX

(71) Applicant: Integra LifeSciences Corporation, Princeton, NJ (US)

(72) Inventors: Gregory J. Pomrink, Bangor, PA (US); Paul K. Alkema, Monroe, NJ (US); Raymond D. Hubbard, Levittown, PA (US); Riyesh Menon, Jersey City, NJ (US)

(73) Assignee: Integra LifeSciences Corporation, Princeton, NJ (US)

( * ) Notice: Subject to any disclaimer, the term of this patent is extended or adjusted under 35 U.S.C. 154(b) by 75 days.

This patent is subject to a terminal disclaimer.

(21) Appl. No.: 17/063,787

(22) Filed: Oct. 6, 2020

(65) Prior Publication Data

US 2021/0085836 A1 Mar. 25, 2021

Related U.S. Application Data

(63) Continuation of application No. 12/771,017, filed on Apr. 30, 2010, now Pat. No. 10,806,833.

(60) Provisional application No. 61/273,741, filed on Aug. 7, 2009, provisional application No. 61/215,875, filed on May 11, 2009.

(51) Int. Cl.
*A61L 33/00* (2006.01)
*A61F 2/46* (2006.01)
*A61K 38/39* (2006.01)
*A61K 9/00* (2006.01)
*C08K 5/00* (2006.01)

(52) U.S. Cl.
CPC ............ *A61L 33/00* (2013.01); *A61F 2/4644* (2013.01); *A61K 9/00* (2013.01); *A61K 38/39* (2013.01); *C08K 5/00* (2013.01)

(58) Field of Classification Search
CPC ........... A61L 15/32; A61L 27/24; A61K 9/00; A61K 38/29; C08K 5/00; A61B 19/00
See application file for complete search history.

(56) References Cited

U.S. PATENT DOCUMENTS

| | | | |
|---|---|---|---|
| 4,841,962 A | 6/1989 | Berg et al. | |
| 5,447,940 A | 9/1995 | Harvey et al. | |
| 5,508,036 A * | 4/1996 | Bakker | A61B 90/00 428/318.6 |
| 5,660,854 A * | 8/1997 | Haynes | A61L 15/64 424/447 |
| 5,776,193 A | 7/1998 | Kwan et al. | |
| 5,997,895 A | 12/1999 | Narotam et al. | |
| 6,352,558 B1 | 3/2002 | Spector | |
| 6,468,308 B1 | 10/2002 | Kuberasampath et al. | |
| 6,716,970 B2 | 4/2004 | Hung et al. | |
| 6,764,517 B2 | 7/2004 | Yamamoto et al. | |
| 6,773,723 B1 | 8/2004 | Spiro et al. | |
| 6,790,454 B1 | 9/2004 | Abdul Malak et al. | |
| 6,896,904 B2 | 5/2005 | Spiro et al. | |
| 6,902,584 B2 | 6/2005 | Kwan et al. | |
| 6,936,276 B2 | 8/2005 | Spiro et al. | |
| 6,939,562 B2 | 9/2005 | Spiro et al. | |
| 7,041,641 B2 | 5/2006 | Rueger et al. | |
| 7,125,967 B2 | 10/2006 | Hung et al. | |
| 7,371,403 B2 | 5/2008 | McCarthy et al. | |
| 7,541,187 B2 | 6/2009 | Myles et al. | |
| 7,683,039 B2 | 3/2010 | Hung et al. | |
| 8,237,009 B2 | 8/2012 | Siniaguine | |
| 9,056,151 B2 * | 6/2015 | Lauritzen | A61L 27/34 |
| 10,806,833 B1 * | 10/2020 | Pomrink | C08K 5/00 |
| 2001/0053839 A1 | 12/2001 | Noishiki et al. | |
| 2002/0169142 A1 | 11/2002 | Jafari et al. | |
| 2003/0040690 A1 | 2/2003 | John Chen et al. | |
| 2003/0181371 A1 | 9/2003 | Hunter et al. | |
| 2004/0078090 A1 | 2/2004 | Binette et al. | |
| 2004/0072756 A1 | 4/2004 | Wilkie et al. | |
| 2004/0175423 A1 * | 9/2004 | Licht | A61K 31/16 424/468 |
| 2004/0220680 A1 | 11/2004 | Yamamoto et al. | |
| 2004/0267362 A1 | 12/2004 | Hwang et al. | |
| 2005/0085924 A1 | 4/2005 | Darois et al. | |
| 2006/0002967 A1 | 1/2006 | Smestad et al. | |
| 2006/0018955 A1 | 1/2006 | DeBusk et al. | |
| 2006/0089719 A1 | 4/2006 | Trieu | |
| 2006/0105026 A1 | 5/2006 | Fortune et al. | |
| 2006/0159732 A1 * | 7/2006 | Cullen | A61L 15/56 424/445 |
| 2006/0194721 A1 | 8/2006 | Allen | |
| 2006/0252981 A1 | 11/2006 | Matsuda et al. | |
| 2006/0293760 A1 | 12/2006 | DeDeyne | |
| 2007/0168044 A1 | 7/2007 | Phillips et al. | |
| 2007/0190101 A1 | 8/2007 | Yang et al. | |
| 2007/0238173 A1 | 10/2007 | Yamagami et al. | |
| 2008/0063627 A1 | 3/2008 | Stucke et al. | |
| 2008/0181950 A1 | 7/2008 | Bates et al. | |

(Continued)

OTHER PUBLICATIONS

Alyanak, Didan, Water Vapor Permeable Membranes, Jan. 2004, Izwir Institute, Masters Thesis, http://library.iyte.edu.tr/tezler/master/biyoteknoloji/T000420.pdf.

*Primary Examiner* — Dah-Wei D. Yuan
*Assistant Examiner* — Andrew J Bowman
(74) *Attorney, Agent, or Firm* — Eva Tan

(57) ABSTRACT

The present invention is directed to an adherent resorbable matrix for use in surgical applications. The adherent resorbable matrix includes a biocompatible adherent material including chitosan.

20 Claims, No Drawings

(56) References Cited

U.S. PATENT DOCUMENTS

| | | |
|---|---|---|
| 2009/0010982 A1 | 1/2009 | Abrthams et al. |
| 2009/0018479 A1 | 1/2009 | McCarthy et al. |
| 2009/0043400 A1 | 2/2009 | Evans et al. |
| 2009/0060975 A1 | 3/2009 | Teets et al. |
| 2009/0087469 A1 | 4/2009 | Zhang et al. |
| 2009/0098176 A1 | 4/2009 | Helmus et al. |
| 2009/0181074 A1 | 7/2009 | Makower et al. |
| 2009/0186062 A1 | 7/2009 | Spector et al. |
| 2009/0280162 A1 | 11/2009 | Wegmann et al. |
| 2010/0028396 A1 | 2/2010 | Ward et al. |
| 2010/0028407 A1 | 2/2010 | Del Priore et al. |

\* cited by examiner

ADHERENT RESORBABLE MATRIX

RELATED CASE INFORMATION

This application is a continuation of U.S. patent application Ser. No. 12/771,071 filed Apr. 30, 2010, now U.S. Pat. No. 10,806,833, which claims priority to U.S. provisional application Ser. No. 61/215,875 filed May 11, 2009 and U.S. provisional application Ser. No. 61/273,741 filed Aug. 7, 2009. The contents of the above applications are hereby incorporated by reference herein in their entireties.

FIELD OF THE INVENTION

The present invention relates to an adherent resorbable matrix for use in surgical applications, for example neurosurgical and orthopedic applications as a dural substitute for the repair and restoration of dural defects in cranial and spinal surgical procedures.

BACKGROUND

Dural substitutes made of resorbable materials are known in the art. Dural substitutes for promoting meningeal tissue growth that include, for example collagen, are described in U.S. Pat. No. 5,997,895. A commercially available resorbable matrix is DURAGEN Dural Graft Matrix (Integra LifeSciences Corporation, Plainsboro, N.J.) Resorbable matrices placed on tissue may migrate out of place during surgery as a result of fluid being present at the site of the matrix, such as blood, cerebralspinal fluid, or irrigation fluid or by contact from the surgeon or surgical instruments. It is desirable to minimize displacement of the resorbable matrix in an in vivo environment, such as during surgery.

It is therefore an object of the present invention to provide an adherent resorbable matrix that adheres to a tissue site in vivo, such as a surgical site, which may come in contact with aqueous fluid. It is also an object of the present invention to provide a resorbable matrix with a material that promotes the adherence of the resorbable matrix to a tissue site in vivo which may come in contact with an aqueous fluid, such as a surgical site. These and other objects, features, and advantages of the invention or certain embodiments of the invention will be apparent to those skilled in the art from the following disclosure and description of exemplary embodiments.

SUMMARY

Embodiments of the present invention are directed to a resorbable matrix that adheres for a period of time to an in vivo site which may include an aqueous fluid, such as a moist body tissue surface. The resorbable matrix includes a material that promotes the adherence of the resorbable matrix to the in vivo site and in the presence of an aqueous fluid, such as blood, cerebralspinal fluid, or irrigation fluid. In the context of embodiments of the present invention described herein, the terms "adherent," "adherence" and "adhesive" are used interchangeably and indicate the property of embodiments of the present invention to resist movement when placed on a tissue surface under influence of fluid being present, force of fluid or force of contact by a surgeon.

According to certain embodiments of the present invention, dural substitutes are provided having increased adhesive capacity. The dural substitute includes a resorbable matrix with a sticky material applied to at least one surface of the matrix. The term "sticky" indicates the property of the embodiments of the invention to resist movement when placed on a tissue surface under influence of fluid being present or force of fluid against the dural substitute or force of contact by a surgeon, and does not necessarily indicate a tackiness of the material as part of a dural substitute. The resorbable matrix can be a matrix sheet made of a biocompatible material, for example, a bioresorbable natural polymer, a bioresorbable synthetic polymer or a combination thereof. The adherent material may be a layer made from any non-cytotoxic, biocompatible chemical or mixture of chemicals, for example, a chemical that is water soluble and is a solid at room temperature in its pure state.

In accordance with another aspect of the invention, there is provided a self adhesive resorbable matrix including an adhesive material that demonstrates an increase in resistance to migration compared to a matrix lacking the adhesive material. The self adhesive resorbable matrix provides a matrix for tissue regeneration that resists migration, due in part to a polysaccharide adhesive layer. In accordance with one aspect, the self adhesive resorbable matrix aids or otherwise promotes fibrin clot formation. Additionally, the self adhesive resorbable matrix provides an adherent regeneration matrix that remains in place and resists movement even in the absence of a fibrin clot or secondary securing devices such as sutures or staples.

In accordance with a further aspect of the invention, there is provided an adhesive resorbable matrix including a biocompatible matrix sheet and a biocompatible adhesive applied on at least one surface of the biocompatible matrix sheet. In more detailed aspects, the biocompatible matrix sheet can be a porous collagen matrix, and the biocompatible adhesive comprises a polysaccharide material and derivatives and modifications thereof. Polysaccharides include, but are not limited to, polysaccharides including free base moieties and salt moieties. One suitable example of a polysaccharide useful in the present invention is chitosan, chitosan derivatives and salts of thereof. Certain chitosan and chitosan derivatives and salts thereof, have a degree of deacetylation in the range of 40-99%. Certain adhesives are crosslinked, partially crosslinked or uncrosslinked as appropriate.

Embodiments of the present invention are also directed to a method of making an adherent resorbable matrix including applying an adherent material, such as in the form of a fluid, slurry or the like, to at least one surface of a resorbable matrix that is to contact tissue which may have a moist or wet surface or otherwise be in an in vivo aqueous environment. The resorbable matrix with the adherent material is then treated to remove the fluid, such as by lyophilization, to create the resorbable matrix with the adherent material thereon.

Embodiments of the present invention are also directed to a method of using an adherent resorbable matrix including applying the adherent resorbable matrix to tissue with a moist or wet surface or otherwise in an in vivo aqueous environment such that the resorbable matrix remains in place, for example with little migration, for a desired period of time.

Other features and advantages of the present invention will become more apparent from the following detailed description of the invention.

DETAILED DESCRIPTION OF CERTAIN EXEMPLARY EMBODIMENTS

Embodiments of the present invention are based on a resorbable matrix characterized in that the resorbable matrix adheres for a period of time to tissue, and may be referred to herein as an adherent resorbable matrix, adhesive resorbable matrix, self adherent resorbable matrix, sticky resorbable matrix or self adhesive resorbable matrix. Embodiments of the adherent resorbable matrix include a resorbable matrix and a material that promotes adherence of the resorbable matrix to the tissue by providing sufficient tack to the resorbable matrix so that the resorbable matrix resists movement when placed on tissue, even under moist, wet or aqueous conditions.

Tissues to which the adherent resorbable matrix can be applied include tissues forming the solid or semi-solid structures that make up any of the organs or compounds of a living organism, preferably human, such as membranes, skin, muscles, bones, cartilage, nerves and nerve sheathes, meninges, connective tissue, blood vessels, the sclera or iris of the eye, the solid materials constituting internal organs such as liver, stomach, pancreas, intestine, kidney, thymus, uterus, testes, bladder, lung, heart and any other internal structures that are solid or semi-solid in texture and including tissues of the gastrointestinal system, the parenchymal organs, the cardiovascular system, the thoracic system, the pulmonary system, the ear, the nose, the throat, the dental area, the gynecological system, the urological system, the vascular system, the bone system, the neurological system, the lymphatic system, the derma, the biliary system and the like.

One component of the self adhesive resorbable matrix is a porous matrix sheet made of a biocompatible material, for example, a bioresorbable natural, semisynthetic or synthetic polymer or a combination thereof. An additional component of the self adhesive resorbable matrix is an adhesive or adherent material which can be in the form of a layer contacting the resorbable matrix and/or partially or wholly impregnated into the matrix or not, on one or both sides of the resorbable matrix when, for example, the resorbable matrix is in sheet form. The self adhesive resorbable matrix can include additional biocompatible components, bioactive agents or other active ingredients.

Both the matrix and the adhesive material forming the self adhesive resorbable matrix are preferably biocompatible and biodegradable. Upon moistening with fluids, the matrix readily conforms to the surface of underlying tissues and when applied with the adhesive contacting tissue, aids in fibrin clot formation and hemostasis along with regeneration of the tissue. Similarly, the adhesive layer also functions to aid in fibrin clot formation and/or hemostasis while facilitating the adherence of the matrix to the tissue to prevent displacement/migration of the device after initial positioning and during surgical irrigation, fixation or other activities. Without wishing to be bound by theory, adhesives having cationic functional groups like protonated amine functional groups, such as with chitosan in acidic or neutral media, react through electrostatic interactions with anionic functional groups in blood proteins and tissue to form a clot. Accordingly, aspects of the present invention include methods of inducing, aiding, promoting, and/or effecting clot formation, such as fibrin clot formation, by applying the adherent resorbable matrix of the present invention to tissue and allowing the interaction between cationic species of the adherent resorbable matrix and anionic species in blood and tissue in a manner to form a clot.

The matrix may include any biocompatible polymer. The biocompatible polymer may be any naturally occurring polymer, a semisynthetic polymer, a synthetic polymer or a combination thereof. For example, the matrix can comprise a material selected from processed animal proteins, tissues or polysaccharides or plant derived polysaccharide or proteins, polymers derived from other living organisms, synthetic materials, or combinations of the aforementioned materials. Useful naturally-occurring biocompatible polymers include fibrous or globular proteins, complex carbohydrates, glycosaminoglycans, and the like or combinations thereof. Certain naturally-occurring biocompatible polymers within the scope of the present invention include collagens, such as collagens of all types, cellulose, gelatin, elastin, alginic acid, hyaluronic acid, versican, desmin, microcellular proteins such as osteonectin, osteopontin, thrombospondin 1 and 2, fibrin, fibronectin, vitronectin, albumin, chitin, chitosan and the like or combinations thereof. According to certain aspects of the present invention, naturally-occurring biocompatible polymers are used as a component for the carrier sheet alone or in combination with other naturally-occurring biocompatible polymers or synthetic polymers. Exemplary biocompatible polymers include heparin, hyaluronic acid, polyhydroxy acid, lactic acid, glycolic acid, copolymers thereof such as PGA/PLA (poly glycolic acid/poly lactic acid), hydroxybutanoic acid, cellulose, gelatin, collagen, chitin, chitosan and the like or a combination thereof. Suitable synthetic biocompatible polymers may include, for example, 2-hydroxyethyl methacrylate, silicone rubber, poly (e-caprolactone) dimethylacrylate, polysulfone, (poly) methyl methacrylate, soluble Teflon-AF, polyethylene terephthalate, nylon, polyvinyl alcohol, polyurethane, polyaminoacids, polydepsipeptides and the like or combinations thereof.

A particular exemplary biocompatible polymer is collagen. Collagen within the scope of the present invention includes collagens from any known class, for example, Class I, II, III, IV, etc. Sources of collagen include mammalian sources, transgenic sources, recombinant sources, and the like or combinations thereof. Exemplary sources include human sources and bovine sources. If the collagen source is a non-human mammal, such as bovine corium or bovine tendon collagen, it is advantageous to inactivate potentially pathogenic agents. According to this aspect, the collagen is greater than 90% pure, substantially free of all prion and viral contamination, has less than 0.03 eu/gm endotoxins, has not more than 5% fat content, has at least 10% hydroxyproline content and has not more than 5% ash content. In an exemplary embodiment of the present invention, the matrix comprises type I bovine collagen, lyophilized into a sponge-like sheet. The collagen matrix aids in the regeneration of the tissue and the adhesive surface reduces the displacement of the matrix after initial positioning and during irrigation or other activities.

The matrix may also include a mixture of biocompatible polymers that biodegrade at different rates. For example, the matrix may include slow-biodegrading collagen and slow-biodegrading polymer, slow biodegrading collagen and fast-biodegrading polymer, fast-biodegrading collagen and slow-biodegrading polymer or fast-biodegrading collagen and a fast-biodegrading polymer. One of skill in the art will readily understand based on the present disclosure that combinations of various biocompatible materials having various degradation rates may be combined to achieve a desired degradation profile for a particular application.

According to certain aspects of the present invention, polymers used to make the matrix, such as collagen, may be crosslinked, partially crosslinked or non-crosslinked. Crosslinking methods include those known to persons of ordinary skill in the art including chemical cross linking, ultraviolet radiation, dehydrothermal cross linking, and the like or combinations of these treatments and for a time period sufficient to achieve a desired degree of crosslinking. Cross linking agents include carbodimide, gluteraldehyde, formaldehyde, diisocyanates, mono, di and polysaccharides, oxidized polysaccharides, enzymes such as genipin and transglutaminase, and the like and mixtures thereof. The degree of crosslinking may range from about 0% (non-crosslinked) to about 100% (fully crosslinked) or any percentage in between (partially crosslinked.) One of skill in the art based upon the disclosure herein will recognize that the degree of crosslinking affects the bioresorption or biodegradation of the collagen. In general, the more highly cross linked the collagen, the longer the collagen may remain within an individual before degradation, for example, weeks, months, and years. Collagen with a low degree of crosslinking can have utility for days or weeks before degradation. Crosslinking can be used to impart a desired stability to the collagen during the intended use of the material. The degree of crosslinking includes from about 0% to about 100%, about 10% to about 90%, or about 15% to about 85% of the reactive functional groups and any ranges and values in between these ranges whether overlapping or not.

The matrix can be fashioned into any desired form or shape, such as a sheet for placement over tissue, a tube within which damaged tissue can be placed or as a mold of a tissue defect site into which the matrix is to be placed. When in sheet form, the sheet should be flexible, comfortable, and of substantially uniform thickness. The sheet should be flexible and readily assume the general shape and contours of the tissues and parts of, for example, the human body to which the sheet is applied. The sheet may also have elastic characteristics allowing it to stretch in one or two directions. The sheet should also be conformable and capable of adapting to the overall shape of the tissues and parts of, for example, the human body, via intimate contact without creating voids or kinks. Further, the sheet may have substantially uniform thickness across its longitudinal (y) and transverse (x) directions.

One skilled in the art would easily recognize that the thickness of the sheet would depend upon the particular application. Typically, the sheet has a thickness of about 0.001 mm to about 100 mm, from about 0.1 mm to about 50 mm, from about 0.3 mm to about 10 mm, from about 0.5 mm to about 10 mm, from about 1.0 mm to about 5 mm, from about 2.5 mm to about 5 mm or about 3 mm and any ranges or value in between whether overlapping or not. The carrier sheet may have any density. One skilled in the art would recognize that the density of the sheet would depend upon the particular application. Typically, the sheet has a density of about 1 mg/cm$^3$ to about 100 mg/cm$^3$.

In one embodiment, a matrix is provided in the form of a collagen sponge. The matrix can also be provided in the form of a non-woven matrix, felt or film according to methods known in the art. The physical structures of a non-woven matrix, felt or film are known to those of skill in the art and can include varying densities, porosities, pore structure, fiber structure and the like depending upon the particular method of manufacture. In addition, composites of the various forms of the matrix can be made such as a film/sponge or a film/sponge/film. A composite of as many layers of a matrix material can be made as desired and according to the desired application. In one aspect of the present invention, a laminate of a collagen sponge and a collagen film is provided. This laminate, which can be formed, e.g., by laminating a collagen sponge to a collagen film with a biocompatible adhesive or polymer (including collagen), by forming a sponge on a film, or by forming a film on a sponge, possess the elevated water impermeability and suturability of a film, and the elevated porosity of a sponge, which facilitates dural tissue growth there through. Similarly, a sandwich-type laminate can be provided by providing a collagen sponge between opposing sheets of collagen film.

The matrix of the present invention includes pores of sufficient size and quantity to permit growing meningeal tissue to infiltrate therein. The pore size ranges, whether internal pores or surface pores, from about 1 µm to about 1000 µm, about 10 µm to about 500 µm, about 30 µm to about 150 µm, about 50 µm to about 300 µm, or from about 50 µm to about 150 µm and any range or value in between the ranges whether overlapping or not.

The porous matrix has a purity defined for medical applications as less than about 100 EU/g. For example, it can have endotoxin levels less than about 40 EU/g. The porous matrix can have a resorption time of between about 0.5 days to about 2 yrs in the human body, for example, in the range of about 30 days to about 180 days.

The matrix can include biocompatible and/or bioresorbable materials other than collagen. For example, in certain embodiments it is advantageous to laminate the collagen matrix to a non-collagen film, such as a 50:50 dl lactide:coglycolide polymer having a molecular weight of about 75,000 and more preferably about 100,000. Additional suitable polymers include, e.g., biocompatible and/or bioresorbable lactides, glycolides, and copolymers thereof, polycaprolactones, polyethylene carbonate, tyrosine polycarboronates, tyrosine polyacids, polyanhydrides and the like. The molecular weight of the polymer is preferably about 5000 to about 500,000.

The adhesive can comprise a natural, semisynthetic or synthetic polymer, a derivative of such polymer, other biocompatible adhesive material, or a combination of two or more of the aforementioned materials. According to one aspect, the biocompatible adhesive can be polycationic polymers, polyanionic polymers, nonionic polymers, salt, protein, fatty molecule, other biocompatible adhesive materials and combinations thereof. An example of a biocompatible adhesive material is a water soluble or a partially water soluble carbohydrate including low, medium and high molecular weight saccharides, such as a monosaccharide, disaccharide or polysaccharide. Such carbohydrates and saccharides include sugars, starches, gums, glycosaminoglycans, celluloses and hemicelluloses and derivatives and modifications thereof.

Adhesive materials within the scope of the present invention have a molecular weight between about 5 kDa and about 2000 kDa, about 10 kDa and about 1500 kDa, about 10 kDa and 1000 kDa, or about 50 kDa and 1500 kDa. Low molecular weight (LMW) adhesive materials may have a molecular weight between about 5 kDa to about 250 kDa or from about 70 kDa to about 150 kDa. Medium molecular weight (MMW) adhesive materials may have a molecular weight between about 250 kDa to about 750 kDa or from about 300 kDa to about 700 kDa. High molecular weight (HMW) adhesive materials may have a molecular weight between about 750 kDa to about 2000 kDa or from about 700 kDa to about 1250 kDa. One of skill will recognize that the present adhesive material can have a molecular weight within any ranges or value within the above ranges whether overlapping or not. One of skill will recognize based on the present disclosure that the molecular weight of the adhesive layer material can depend on the particular adhesive formulation and the desired adhesive property. Suitable adhesives can be applied in an amount between about 1% and about 99%, between about 25% and about 75%, or between about 40% and about 60% of the total weight of the adherent resorbable matrix.

Suitable adhesives according to certain embodiments include water soluble or partly water soluble free base forms and/or salt forms of carbohydrates and saccharides. Examples of acceptable salts include, but are not limited to, mineral or organic acid salts of basic residues such as amines; alkali or organic salts of basic residues such as carboxylic acids; and the like. The acceptable salts include the conventional non-toxic salts or the quaternary ammonium salts from non-toxic inorganic acids. For example, such conventional non-toxic salts include those derived from inorganic acids such as hydrochloric, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmoic, maleic, hydroxymaleic, phenylacetic, glutamine, benzoic, salicylic, sulfanilic, 2-acteoxybenzoic, fumaric, toluenesulfonic, methanesulfonic, ethane disulfonic, oxalic, isethionic, and the like. Specifically, the acceptable salts can include those salts that naturally occur in vivo in a mammal. According to certain embodiments, exemplary salts are those formed from acids having a pKa of between about 1.5 and 8.5. Exemplary salts also include those formed from acids having a pKa of between about 2.5 and about 6.5 or between about 4.0 and 6.0. A particular exemplary salt includes that formed from acetic acid which has a pKa of about 4.7. One of skill in the art based on the benefit of this disclosure will readily be able to identify acids having a pKa of within the above ranges using reference materials available to one of skill in the art such as tables listing acids and their pKa values.

One example of a polysaccharide useful in the present invention is water soluble chitosan, According to one embodiment, a polysaccharide useful in the present invention includes chitosan having a degree of deacetylation between about 40% and about 99%, a percent of amine-based salt moieties between about 0% and about 100% and molecular weight range between about 50 kDa and 2000 kDa or any range or value within that range whether overlapping or not as described above. The adhesive materials can also be chitosan derivatives such as carboxymethyl chitosan, hydroxyl propyl chitosan and the like or salts of such derivatives such as salts of carboxymethyl chitosan, hydroxyl propyl chitosan and the like.

According to certain exemplary embodiments, chitosan within the scope of the present invention can have a degree of deacetylation between about 40% and about 99%, between about 40% and about 93%, between about 40% and about 75%, between about 45% and about 80%, between about 50% and about 70%, between about 55% and about 75%, between about 50% and about 65%, or between about 50% and about 60% or within any range or value within the above ranges whether overlapping or not. According to one embodiment, the degree of deacetylation is less than about 65%, less than about 60%, or less than about 55%.

According to an additional aspect of the present invention, the chitosan is yellow in color and thereby provides a natural color indicator of the side of the self adherent matrix to contact tissue and adhere. It is to be understood that coloring ingredients, such as blue dye, could be added to either the matrix or adhesive material to further distinguish the side of the self adherent matrix to contact tissue and adhere. In this manner, a method is provided to identify an adhesive portion of an adherent resorbable matrix intended to contact a tissue site by utilizing color to distinguish the adhesive portion from the matrix portion. In this manner, the adhesive portion is identified by a particular color, which may be the natural color of the adhesive or which may be due to the addition of a coloring agent such as a dye and an individual applying the adherent resorbable matrix will contact the adhesive portion having the particular color to intended tissue. In a certain embodiment, the matrix portion is identified by a particular color which may be the natural color of the matrix or which may be due to the addition of a coloring agent such as a dye. Each of the adhesive portion and the matrix portion may include a coloring agent to alter the color from the natural color of the adhesive portion and the matrix portion. According to an exemplary embodiment, the color of the adhesive portion is different from the color of the matrix portion, so as to distinguish each portion. A coloring agent may be added to the adhesive portion and/or the matrix portion in whole or in part. For example, the entire adhesive portion may be the same color such as when a colorant is added during the manufacturing process and mixed homogeneously into the adhesive formulation prior to applying the adhesive formulation to the matrix. Similarly, the entire matrix portion may be the same color such as when a colorant is added during the manufacturing process and mixed homogeneously into the matrix formulation prior to lyophilization to firm the solid matrix. According to alternate embodiments, only certain portions of the adhesive portion and/or the matrix portion may be colored. For, example, a colored pattern may be applied to the surface of either the adhesive portion or the matrix portion in any desired pattern such as dots, stripes, etc. Any printing technique known to those of skill in the art, such as application by hand or spray, silk screen printing, stamping, ink jet, etc. is useful in the present invention. Similarly, a coloring agent may be used to print images or words onto the surface of either the adhesive portion or the matrix portion, such as "Up," "This Side Up," "Apply This Side Away From Dura," "Down," "This Side Down," or "Apply This Side To Dura." Coloring agents may be any coloring agents known to those of skill in the art as indicated safe for human or animal consumption or safe for introduction into a human or an animal. One of skill would readily identify such coloring agents from publicly available reference materials. Coloring agents may have any color such as red, orange, yellow, green, blue, indigo, violet or any combinations or shades or hues of these colors. Accordingly, one aspect of the present invention is directed to an adhesive resorbable matrix including a visible indicator to distinguish between the adhesive portion and the matrix portion. Such an adhesive resorbable matrix is useful in a method of applying the matrix to tissue described herein including the additional step of confirming through visual recognition the visible indicator and placing the portion of the adherent resorbable matrix with the visual indicator in contact with or away from tissue.

According to certain aspects, one or more amine base units of chitosan are reacted with an acid to form a salt moiety. In this manner, the chitosan having salt moieties may be considered a chitosan salt. In a similar manner, the chitosan has a salt content insofar as it includes salt moieties. According to certain other aspects, one or more amine base units of chitosan are reacted to form a salt moiety with an acid having a pKa of between about 1.5 and 8.5, or with an acid having a pKa of between about 2.5 and 6.5, or with an acid having a pKa of between about 4.0 and 6.0. One of skill in the art will recognize that the amount of salt moieties is dependent upon the pKa of the acid and chitosan along with the final pH of the solution. Salt substitution can change simply by changing the pH of the solution. Similarly, base moieties of other adhesive materials within the scope of the present invention can similarly be reacted with an acid to form salt moieties. A particular exemplary acid used to form a salt with one or more amine groups of chitosan is acetic acid which has a pKa of about 4.7. According to one aspect, one or more acids with one or more different pKa values can be reacted with the amine groups of chitosan to form various different salt moieties. For example, a mixture of acetic acid and lactic acid can be used to react with amine groups of chitosan to form different salt moieties on the chitosan. One of skill in the art based on the benefit of this disclosure will readily be able to identify acids having a pKa of between about 1.5 and 8.5, a pKa of between about 2.5 and 6.5 or a pKa of between about 4.0 and 6.0 using reference materials available to one of skill in the art such as tables listing acids and their pKa values. Such exemplary tables of dissociation constants and pKa of organic acids in aqueous solutions and inorganic acids in aqueous solutions are found in the CRC Handbook of Chemistry and Physics 55$^{th}$ Edition (1974-1975) at D-129 to D-130 hereby incorporated by reference. Other reference materials are known to exist to those of skill in the art to identify pKa values for acids.

In addition, one of skill in the art will understand that the percent of salt moieties in chitosan may depend upon pH. Without wishing to be bound by theory, for example, for chitosan, at a pH of about 8 to about 8.5, the ratio of salt to free base is about 0.03 to 1. When at a pH of about 5, the ratio of salt to free base is about 30 to 1. At a pH of about 6.5, the ratio of salt to free base is about 1 to 1. Accordingly, the percent of salt moieties created by acid reaction to total amine groups before acid reaction ranges from about 0% (in the case of all or substantially all of the amines being in the free base form) to about 100% (in the case of all or substantially all of the amines being reacted to salt groups). The term chitosan free base can include some degree of neutralization of acid with the amine groups to yield salt groups, forming a water soluble or partially water soluble compound. The term chitosan salt can include some degree of amine groups present on the chitosan. In additional exemplary embodiments, the percent of salt moieties can range from between about 1% to about 99%, about 3% to about 99%, about 10% to about 90%, about 10% to about 80%, about 20% to about 80%, about 30% to about 70%, from about 40% to about 60%, from about 45% to about 55%, about 50% (i.e., a ratio of salt to amine of about 1 to 1) and any ranges and value in between whether overlapping or not. One of skill in the art will understand that acids may be used that are sufficient to make a salt and a resulting water soluble or partly water soluble polymer salt with any sufficient percent of salt moieties converted from base moieties.

According to certain embodiments, the chitosan free base has a solubility in water at 25° C. ranging from 0.01% to 99.9% dependent at least in part on viscosity and molecular weight, for example, a solubility of about 1 to about 25%. According to certain embodiments, the chitosan free base has a purity defined for medical applications as less than about 100 EU/g. For example, it can have endotoxin levels less than about 40 EU/g. According to certain embodiments, the chitosan free base can have a resorption time after positioning and hemostasis of about 1 to about 60 days in the human body, for example, a resorption time of about 3 to about 30 days, followed by resorption of the porous matrix between about 0.5 days to about 2 years, for example about 30 days to about 180 days, as tissue is regenerated. The resorption is controlled by the molecular weight of the free base or salt in conjunction with the composition and extent of crosslinking of the matrix.

According to certain embodiments, the chitosan salt or chitosan derivative salt can be organic or inorganic acid salts of chitosan or chitosan derivatives, for example, inorganic salts from the group of halides (F, Cl, Br, I), organic salts from amino acids or low MW organic acids, and diacids with these materials consisting of up to 12 carbon atoms. Examples include, but are not limited to, chitosan chloride, chitosan glutamate, chitosan ascorbate, chitosan lactate, chitosan malate, chitosan acetate, and other pharmaceutically acceptable salts of chitosan or chitosan derivatives. According to one embodiment, the chitosan salt is a hydrogen chloride, glutamic acid or a lactic acid salt.

In further detailed aspects, the biocompatible adhesive can be a cellulose, such as a modified cellulose including, for example, hydroxypropyl methyl cellulose. According to an additional embodiment, a biocompatible adhesive material includes a nonionic polymeric polysaccharide (including one of hydroxyethyl cellulose and carboxymethyl cellulose), a synthetic nonionic polymer (including one of polyvinyl pyrrolidone, polyisobutylene, polyethylene glycol dimethyl ether, polysuccinimide, reverse phase matrix, poly (ethylene oxide), and polyvinyl alcohol hydrolized), a nonionic fatty compound (including one of alpha-tocopherol), a polyanionic polysaccharide (including one of hyaluronic acid, chondroitin sulfate, oxidized dextran, oxidized starch, chondroitin sulfate N-hydroxysuccinimidyl ester, carageenan, cellulose cyanoethylated, xantham gum, and guar gum), a synthetic polyanionic polymer including polyacrylic acids and polyacrylic acid polymers, a polycationic polysaccharide (including one of chitosan oligosaccharide lactate), a synthetic polycationic polymer (including one of polydiallyldimethyl ammonium chloride, poly (acrylimide-co-diallymethyl ammonium chloride), polyethyleneimine, and polycarbodiimide), a polycationic peptide (including one of albumin and poly 1-lysine hydrobromide), a salt (including one of calcium chloride and sodium tetraborate), or a protein (including one of gelatin, thrombin, and fibrinogen) and combinations and modifications thereof.

A bioactive agent may be included in the adherent resorbable matrix, such as in either the matrix or the adhesive material or both. The bioactive agent may include, for example, a neurotransmitter, a hormone, an immunomodulator, an immunosuppressant, an antibiotic, a cytostatic, a dirurectic, a gastrointestinal agent, a cardiovascular agent, a neuropharmaceutical, a blood coagulation inducing agent, and the like or a combination thereof. The matrix or adhesive preferably includes effective amounts of meningeal tissue growth factors and/or bioactive peptides, such as, e.g., RGD containing peptides, decorin, laminin, merosin, chondroitin sulfate, dermatin sulfate, heparin (bFGF), fibronectin and other integrin ligands, entactin, tenascin and the like. In certain embodiments, an effective amount of such an additive is about 1 ug/mg matrix material such as 1 ug/mg collagen.

The bioactive agent may also include, for example, any drug, metabolite, or prodrug thereof, organic compound, substance, nutrient or biologically beneficial agent including proteins, peptides (including polypeptides and oligopeptides), hormones, vaccines, oligonucleotides, genes, nucleic acids, steroids, antibiotics, antibodies, viruses, live cells, and other chemotherapeutic or non-therapeutic agents, or a combination thereof.

Suitable bioactive agents may also include, for example, a regenerative agent such as one or more human growth factor-b, fibroblast growth factor or vascular endothelial growth factor; or the agent may be a gene therapy agent, a cogener of platelet derived growth factors; or a monoclonal antibody directed against growth factors; or the agent may be a drug, a cell regeneration factor, drug-producing cells, or regenerative cells.

Due to the abundance of cationic amino groups along the structure of chitosan, it is known that the drugs with carboxyl groups may be conjugated thereto and sustained release can be achieved through the hydrolysis of the amide or ester bonds linking drugs to the chitosan molecule. As a polyelectrolyte, chitosan can electrostatically conjugate sensitive bioactive agents (e.g., recombinant proteins, such as VEGF) while preserving their bioactivities and enhancing their stabilities.

Suitable bioactive agents may further include, for example, progenitor cells of the same type of those from the vascular site, for example, an aneurysm, and progenitor cells that are historically different from those of the vascular site such as embryogenic or adult stem cells, which can act to stabilize the vasculature and/or accelerate the healing process. These cells may be incorporated into the matrix, the adhesive, or both the matrix and the adhesive.

Additional bioactive agents may include, for example, one or more supplements, such as growth factors, polyclonal and monoclonal antibodies, and other compounds. Illustrative examples of such supplements include, for example, the following: fibrinolysis inhibitors, such as aprotonin, tranexamic acid and e-amino-caproic acid; antibiotics, such as tetracycline and ciprofloxacin, amoxicillin, protein C, heparin, prostacyclins, prostaglandins (particularly (PG1), leukotrienes, antithrombin III, ADPase, and plasminogen activator, steroids, such as dexamethasone, inhibitors of proptacyclin, prostaglandins, leukotrienes and/or kinins to inhibit inflammation; cardiovascular drugs, such as calcium channel blockers, vasodilators and vasoconstrictors; chemo attractants; local anesthetics such as bupivacaine; and antiproliferative/antitumor drugs such as 5-fluorouracil, taxol and/or taxotere; antivirals, such as gangcyclovir, zidovudine, amantidine, vidarabine, ribaravin, trifluridine, acyclovir, dideoxyuridine and antibodies to viral components or gene products; cytokines, such as alpha- or beta- or gamma-Interferon, alpha- or beta-tumor necrosis factor, and interleukins; colony stimulating factors, erythropoietin, antifungals, such as diflucan, ketaconizole and nystain; antiparasitic agents, such as pentamidine; anti-inflammatory agents, such as alpha-1-anti-trypsin and alpha-1 antichymotrypsin; anesthetics, such as bupivacaine; analgesics; antiseptics; hormones; vitamins and other nutritional supplements; glycoproteins; fibronectin; peptides and proteins, carbohydrates (both simple and and/or complex); proteoglycans; antiangiogenins; antigens; lipids or liposomes; oligonucleotides (sense and/or antisense DNA and/or RNA); and gene therapy reagents.

The amount of bioactive agent incorporated into either the matrix or adhesive material or both depends upon the desired release profile, the concentration of bioactive agent required for a biological effect, and the length of time that the bioactive agent has to be released for treatment, and should be within the discretion and wisdom of the patient's attending physician. There is no upper limit on the amount of bioactive agent incorporated into the biocompatible adherent sheet. The lower limit of bioactive agent incorporated into the biocompatible adherent sheet is dependent upon the activity of the bioactive agent, and the length of time needed for treatment. Specifically, in one embodiment, the biocompatible adherent sheet can be formulated to provide a one month release of bioactive agent. Alternatively, in another embodiment, the biocompatible sheet can be formulated to provide a three month delivery of bioactive agent. The biocompatible adherent sheet should release the bioactive agent contained within the biocompatible adherent sheet at a controlled rate until the biocompatible adherent sheet is effectively depleted of bioactive agent.

The adherent resorbable matrix provides a highly porous matrix for the infiltration of cells (i.e. fibroblasts) and a substrate for the deposition of new collagen upon implantation. The porous structure of the matrix facilitates the ingrowth of cells (i.e. fibroblasts) into the regenerative matrix. The device is gradually resorbed and replaced by endogenous connective tissue. The resorption depends on factors such as the molecular weight of the cationic polysaccharide free base or salt and the composition and extent of crosslinking of the matrix.

The self adhesive resorbable matrix can be used for neurosurgical and orthopedic applications as a dural substitute for the repair and restoration of dural defects in cranial and spinal surgical procedures. It can also be used in neurosurgical and orthopedic applications to close dural defects following traumatic injury, excision, retraction, or shrinkage, or as a supplement to primary closure in cranial and spinal surgical procedures. Other applications include, but are not limited to, wound, hernia repair, breast reconstruction, adhesion prevention, tendon/vessel protection, and other soft tissue repair. The adherent resorbable matrix may be used to close soft tissue defects from diabetic ulcers, tunneling wounds, burns, traumatic injury or surgery and may function as primary closure or an adjunct to primary closure.

According to certain embodiments, a thin layer of a chitosan free base and/or chitosan salt such as an inorganic chitosan salt (such as a chitosan chloride, chitosan bromide, chitosan iodide or chitosan fluoride salt) or an organic chitosan salt (including one of chitosan lactate, chitosan acrylate, chitosan malate, chitosan acetate or chitosan glutamate), between about 1 and about 60% of the total mass of the adherent resorbable matrix and with a molecular weight of about 10 to about 2000 KDa, for example about 50 to about 150 kDa, is evenly spread on one side of the highly biocompatible, porous, high purity matrix. Chitosan free base, inorganic chitosan salts or organic chitosan salts and mixed chitosan salts are commercially available from Adjuvant Pharmaceuticals (Adjuvant), Alpharetta, Ga. Chitosan chloride is available from FMC BioPolymer (Ewing, N.J.) or Carbomer (CA). The chitosan free base, inorganic chitosan salt or organic chitosan salt is reconstituted to an about 0.1 to about 50 weight percent solution by solubilizing in deionized or other purified water. The solution is applied to the matrix using known methods and techniques.

The self adhesive resorbable collagen matrix can be cut into the desired shape for use in the surgical site and can readily conform to the surface of the underlying tissues. The self adhesive resorbable collagen matrix may be used to close or seal soft tissue defects following traumatic injury, excision, retraction or shrinkage and may also be used to supplement primary closure. The self adhesive resorbable collagen matrix maintains its position in a wet field upon exposure to blood, CSF and irrigation. According to embodiments of the present invention, the adherent resorbable matrix is used to repair two physically noncontiguous tissues or portions thereof that are to be joined together, or where a hole, tear, cut, perforation, or other discontinuity is repaired so as to close the hole, tear, cut or perforation. The adherent resorbable matrix has at least some degree of adhesion to the tissue to which the biocompatible adherent sheet is applied, such that the sealed tissue is secured against at least a moderate displacing force. The discontinuity in the tissue that is being sealed may be an incision made as part of a surgical procedure, or it may be a wound.

In certain embodiments, the adherent resorbable matrix is indicated for application to a moist environment with limited liquid or body fluids. In one embodiment, application of the adherent resorbable matrix requires gentle pressure for approximately 10 seconds. The tackiness of the adhesive layer when exposed to a moist environment is characterized by an increase in uniaxial tensile adhesion (using for example ASTM F-2258-05) from about 0.4N to about 10N as compared to less than 0.4 N for a matrix without an adhesive layer. In simulated application to a vertical surface of protein rich substance (sausage casing, Nippi Inc., Tokyo, Japan), the adherent resorbable matrix of the present invention exhibited a resistance to migration for up to 180 seconds under a continuous flow of water or saline at 30-40 ml/s. In comparison, the average resistance to migration of a single layer collagen matrix without an adhesive is less than one second.

According to other embodiments, the adherent resorbable matrix is suitable for repairing intentional damage to the meningeal tissues, as in surgery, and consequential damage to the meningeal tissues, as might occur as a result of accidental head trauma. For example, after brain surgery, the adherent resorbable matrix of the present invention is inserted to occupy space left by the removal resultant on surgery. As to meningeal repair following a craniotomy or a laminectomy, particularly with the incision through the dura, the adherent resorbable matrix of the present invention can simply be implanted on contact with the cranial or spinal dural defect created by the surgery. Although it can be preferred to simply contact the damaged meningeal tissue and adjacent undamaged tissue with the adherent resorbable matrix (particularly when the adherent resorbable matrix is being used as a cranial dura substitute), the product can also be mechanically bonded (e.g., sutured) and/or chemically bonded to the damaged tissue and adjacent undamaged tissue (e.g., fibrin glue). The adherent resorbable matrix preferably connects undamaged portions of meningeal tissue adjacent to the damaged meningeal tissue by overlapping these undamaged tissues. The damaged tissue can be, e.g., torn, cut, excised or lacerated, and can be located in e.g., the human spinal dura or the human cerebral dura. Regenerated meningeal tissue grows within the product, while the product remains implanted within a patient. That is, the product acts as a matrix or scaffold for tissue growth, such as for reparative tissue growth. According to certain embodiments, the product is sustainably resorbed within about three months after implantation. Although the product of the invention is particularly suitable for dural repair, it is also suitable for promoting tissue growth and/or wound healing in other contexts. For example, the product is suitable for use as a bioresorbable pledget to assist in suturing, a suturable hemostatic device, hernia patches, pericardial patches, and the like.

Accordingly, the adherent resorbable matrices of the present invention have neurosurgical and orthopedic applications as a dural substitute for the repair and restoration of dural defects in cranial and spinal surgical procedures. The adherent resorbable matrices of the present invention have neurosurgical and orthopedic applications to close dural defects following traumatic injury, excision, retraction or shrinkage. The adherent resorbable matrices of the present invention have neurosurgical and orthopedic applications as a supplement to primary closure in cranial and spinal surgical procedures. The adherent resorbable matrices of the present invention have applications in wound repair, hernia repair, breast reconstruction, tissue adhesion prevention, tendon and/or vessel protection and other soft tissue repair.

The following examples are specific embodiments of the present invention but are not intended to limit it.

Example 1

Preparation of an Exemplary Matrix

A matrix according to the present invention including a bioresorbable natural, semisynthetic or synthetic polymer or a combination thereof is prepared according to the following method using bovine collagen as an exemplary polymer to form a matrix having sponge-like characteristics. The method includes steps that are recognized as effective for inactivating viral and prion contamination, thereby increasing safety and reducing inflammatory response. According to one embodiment, the matrix is substantially free of viruses and prions without being physiologically incompatible. The phrase "substantially free of viruses and prions" means that the product does not contain infection-effective amounts of viruses and prions. In one aspect, collagen is treated by a process sufficient to achieve at least a 4 log clearance of virus, or at least a 6 log clearance of virus, or at least an 8 log clearance of virus, as measured with a statistical confidence level of at least 95%. For example, if the concentration of virus before treatment is $10^7$ and after treatment is $10^1$, then there has been a 6 log clearance of virus.

In general, a self adhesive resorbable collagen matrix can be prepared by providing a collagen dispersion slurry; lyophilizing the collagen slurry until moisture is removed to produce a collagen sheet (or other desired shape or form); cross-linking the lyophilized collagen sheets; making an aqueous solution of an adhesive; applying the adhesive solution onto the lyophilized and cross-linked collagen sheets; and lyophilizing the sheet to produce the self adhesive resorbable collagen matrix. The self adhesive resorbable collagen sheet can be cut into the desired size and shape, packaged, and sterilized for commercialization.

More particularly, the adhesive matrix can be prepared by applying a thin layer of an inorganic or organic salt or a water soluble or partially water soluble free base or some combination thereof of the cationic (chitosan) polysaccharide adhesive (between 1 and 60% of the total mass of the device) evenly or in an intermittent pattern over one or more sides of the porous collagen matrix. The cationic polysaccharide free base or salt component is reconstituted to an about 1 to about 40 weight percent solution by solubilizing the sheet, powder or granules in deionized or other purified water or polar protic solvent or polar aprotic solvent or some combination thereof. The adhesive is applied as a mixture, slurry or solution to the collagen matrix manually using a spatula, draw-down bar, spraying, or similar method directly onto the matrix or the adhesive material may be applied to a rigid surface and subsequently transferred to the porous matrix. An adhesive solution may also be applied using a patterned grid over the surface of the matrix and spreading the adhesive solution over the grid, delivering the solution to a specific percentage of the surface area with a known volume delivered. In the liquid form the adhesive is allowed to partially absorb into the surface of the porous matrix through capillary action. The extent of the adhesive penetration into the matrix is thermally controlled whereas the construct is rapidly frozen at specific time points to arrest the process. The device is then lyophilized using standard methods for a minimum of 6 hours or until completely dried. The dry device is cut, packaged in double blister or foil packaging, and exposed to ethylene oxide gas, electron beam, or gamma irradiation for sterilization.

In accordance with the present invention, a collagen dispersion is prepared according to methods well known in the art. A native source of Type I collagen, such as skin, tendons, ligaments or bone, is first mechanically or hand cleaned of fat, fascia and other extraneous matter and washed. The cleaned and washed collagen containing material is then comminuted, generally by slicing or grinding. The material is then subjected to an enzyme treatment while under intermittent stirring with a proteolytic enzyme, such as ficin, pepsin, and the like, so as to remove non-collagenous impurities which may cause antigenic activity and to swell the collagen by removing elastin. The amount of enzyme added to the collagen material and the conditions under which enzyme digestion takes place is dependent upon the particular enzyme being used. Generally, when using ficin, which is most commonly used, the pH is adjusted to about 6.0 to 6.3, and the collagen material is digested for about 1 to 2 hours at a temperature of about 36.5° C. to 37.5° C. with one part ficin for every 150 parts of collagen material. After the requisite amount of time, the enzyme is inactivated by appropriate means well known in the art, such as by the addition of a solution of an oxidizing agent, such as sodium chlorite when the enzyme is ficin. The enzyme treated collagen containing material is then washed to remove excess enzyme and the non-collagenous protein impurities. Preferably, the washing is carried out with ultra-filtered and deionized water and optionally further washed with dilute aqueous hydrogen peroxide.

The enzyme digested collagen containing material is then further subjected to an alkali treatment at a pH of about 13 to 14, at a temperature of about 25° C. to 30° C. for a period of about 35 to about 48 hours. An exemplary period is about 40 hours. The alkali treatment is carried out in an aqueous solution of 5% sodium hydroxide and 20% sodium sulfate. This alkali treatment removes contaminating glycoproteins and lipids. The solution is then neutralized with a suitable acid, such as aqueous sulfuric acid, and thoroughly washed. The collagen material is then further swollen with a suitable acid solution which acid does not cause any cross-linking of the collagen. Such acids are well known to those skilled in the art and include acetic acid, hydrochloric acid, lactic acid, and the like. Regardless of which acid is used, the pH of the acid collagen dispersion is in the range of about 2 to 3.

The dispersed collagen mixture is then homogenized by any conventional means, such as a blender or homogenizer, so as to further dissociate the fibers and is then filtered to remove unswollen, non-collagenous material by means well known in the art, such as by passing the dispersion through a 100 mesh stainless steel screen. The resulting filtered collagen dispersion can then be used to prepare the matrix of the present invention.

The matrix can be prepared by lyophilization of a collagen dispersion prepared according to the patent, preferably having a concentration of between 0.1 and 10% solids (w:w) and more preferably at least 1.0% solids. A volume of the dispersion is poured into a suitable (preferably non-stick) tray to provide a matrix having a suitable shape. The matrix has a thickness from about 2.5 mm to about 5 mm. An exemplary thickness is about 3 mm. The dispersion is then frozen and lyophilized for about 1 to about 48 hours. The density of the dispersion and the lyophilization cycle affect the matrix density and pore size. The matrix density is about 0.0001 mg/mm$^3$ to about 0.12 mg/mm$^3$. An exemplary density is about 0.009 mg/mm$^3$.

The matrix of the present invention has sponge-like properties and can be referred to as a sponge. The matrix of the present invention includes pores of a sufficient size and quantity to permit growing meningeal tissue to infiltrate therein. The pore size ranges from about 10 μm to about 500 μm, and about 50 μm to about 150 μm, with surface pores being smaller than cross-sectional (internal) pores. In certain exemplary embodiments, the surface pores range in diameter from about 30 μm to about 150 μm. An exemplary surface pore size is about 70 μm. The cross-sectional pores range in diameter from about 50 μm to about 300 μm. An exemplary cross-sectional pore size is about 70 μm.

Example 2

Preparation of an Adhesive Solution and Application to a Matrix

The adhesive can be applied in any desired pattern on one or more surfaces of the matrix that are to contact tissue. One of skill in the art, given the geometry of the matrix and its intended application, will understand where adhesive is to be applied given the portion of the matrix that is to contact tissue. For example, if the matrix is in the form of a sheet, the adhesive material can be applied to one or both surfaces given the desired utility of the sheet. According to certain aspects, the adhesive layer can have a thickness of between about 0.10 mm to about 1 mm, about 0.12 mm to about 0.8 mm, about 0.18 to about 0.6 mm, from a bout 0.2 mm to about 0.5 mm, from about 0.3 mm to about 0.4 mm and any ranges or value within the above ranges whether overlapping or not. One of skill will recognized based on the present disclosure that the thickness of the adhesive layer can depend on the particular adhesive formulation and the desired adhesive property.

According to one aspect, a thin layer of the adhesive (between 10 and 40% of the total mass of the device) is evenly spread onto one side of a lyophilized collagen sponge. Adhesive materials within the scope of the present invention, such as chitosan having a molecular weight of about 75 kDa to about 600 kDa and a degree of deacetylation of about 50% to about 55% and chitosan chloride salt are commercially available from sources such as Adjuvant and FMC respectively and are reconstituted to an about 1 to about 50 weight percent solution, about 3 to about 40 weight percent solution, about 5 to about 20 weight percent solution and any ranges or values therein whether overlapping or not, by solubilizing the adhesive material in deionized or other purified water. The solution is applied to the collagen matrix by an appropriate method known in the art, for example, by hand using a spatula or drawdown bar method. Partial absorption of the solution including the adhesive material into the top layer of the collagen sponge is thermally controlled. It is to be understood that higher weight percent adhesive material solutions are generally more viscous and thus tend to absorb less into the surface of the matrix material. Higher weight percent adhesive material solutions also create a more dense adhesive layer when lyophilized. The device is then lyophilized (Virtis or other lyophilizer) for a period of time such as 12 hours or until completely dried. The dry device is cut, packaged in double blister packaging, and exposed to ethylene oxide gas for sterilization.

Chitosan materials having acetate salt groups used in the examples were purchased from Adjuvant Pharmaceuticals L.L.C., Marietta, Ga. The chitosan materials in the examples are indicated as being LMW (low molecular weight), MMW (medium molecular weight) or HMW (high molecular weight.) Chitosan materials designated as LMW were obtained from Adjuvant LOT #109-002 and were characterized as follows: Appearance: off white powder; Viscosity as measured by a Brookfield Viscometer in a 1% solution in 1% acetic acid: 4 CPS; Weight Loss on Drying 1 g at 60° C. in vacuum oven, ON: 2%; pH in a 1% aqueous solution: 5.3; GPC Molecular Weight: 100 kDa; Degree of Deacetylation as determined by NMR: 55%; and Protein Content: 0.04%. Chitosan materials designated as MMW were obtained from Adjuvant LOT #88-56 and were characterized as follows: Appearance: off white powder; Viscosity as measured by a Brookfield Viscometer in a 1% solution in 1% acetic acid: 45 CPS; Weight Loss on Drying 1 g at 60° C. in vacuum oven, ON: 3%; pH in a 1% aqueous solution: 5.0; GPC Molecular Weight: 696.3 kDa; Degree of Deacetylation as determined by NMR: 60%. Chitosan materials designated as HMW were obtained from Adjuvant LOT #109-018 and were characterized as follows: Appearance: off white powder; Viscosity as measured by a Brookfield Viscometer in a 1% solution in 1% acetic acid: 12.8 CPS; Weight Loss on Drying 1 g at 60° C. in vacuum oven, ON: 5%; pH in a 1% aqueous solution: 5.5; GPC Molecular Weight: 1000 kDa; Degree of Deacetylation as determined by NMR: 50%; Endotoxins: 9 EU/gram and Protein Content: 0.04%.

A exemplary method to create a viscous, aqueous solution from commercially available chitosan powder and to coat a collagen matrix with the aqueous solution is as follows. Chitosan is a water-soluble powder and is a solid at room temperature in its pure state. Chitosan can be dissolved at a known concentration in WFI product water to create an aqueous solution of chitosan. A 1% solution of chitosan is prepared and the viscosity determined. Exemplary amounts of chitosan added to produce a desired weight percent solution are presented in Table 1 below.

TABLE 1

| 1 wt % Viscosity | 3-6.99 cps | 7-12.99 cps | 13-19.99 cps | 20-26.99 cps | 27-50 cps |
|---|---|---|---|---|---|
| Viscosity of solution | 18 wt % | 15 wt % | 12 wt % | 9 wt % | 6.5 wt % |
| Chitosan to add per 1 ml water (C) | 0.18 grams | 0.14 grams | 0.10 grams | 0.09 grams | 0.065 grams |

Determine a desired volume of solution (B). Place 250 ml beaker on a stir plate. Using a pipette gun and 50 ml pipette, fill the beaker with the volume of WFI product water determined above (B). Place stir bar in water and stir at 300 rpm. Using the determined viscosity, determine chitosan mass value (C) from Table above, and measure out appropriate mass of chitosan to prepare a 6.5-18 wt % solution as determined below. The mass of chitosan in solution (D) is determined by multiplying B by C. Add chitosan slowly to stirring water, allowing time to dissolve. As necessary, stir by hand with spatula and/or adjust stir bar rotation to achieve even stirring. Weight percent solution created is equal to D/B*100%. Continue stirring until no dense powder clumps can be visualized. Place solution in 2-8° C., covered with parafilm until needed.

An 18 wt % aqueous chitosan solution is applied to a collagen sponge matrix as follows. For purposes of creating a thin (0.3 mm) water-soluble coating, chitosan can be dissolved at a known concentration in deionized water and spread evenly across 22 in×20 in×3.5 mm dry and vapor crosslinked sheets of collagen matrix made of 1.0% solids alkali dispersion. In manual mode, initiate freeze mode on a lyophilizer with temperature set point set to −40° C. Allow at least 1 hour to elapse before continuing to ensure that the lyophilizer is at the set temperature before loading. Place 8 in×10 in HDPE sheet on hard, flat surface. Align 300 micron draw down bar at the end of the rigid surface secured by the 1 kg mass. Cut sheets of in process alkali sheets of collagen sponge into equal quarters, yielding four (4) equal sized sponges, approximately 8 in×10 in. Record the "pre-mass" of each sheet in a log. Remove chitosan solution from 2-8° C. storage and allow several hours to come to room temperature. Pour approximately 25 ml of chitosan solution from its container and spread on the plastic sheet in a line in front of the draw down bar. Grasp the 300 micron drawn bar by both handles and draw down the solubilized chitosan in a thin film across the plastic sheet. Allow at least 5 seconds for the material to self-level. Place the smooth side of the collagen alkali sheet against the thin film of chitosan. Place a 10 in×12 in stainless steel mesh on top of the sample for gentle, even pressure against the layer of chitosan. Wait 2 minutes and remove the 10 in×12 in mesh. Transfer the 10 in×12 in tray with sample immediately to a lyophilizer with shelves pre-frozen to −40° C. freezer. The sample should contact the lyophilizer 2-2.5 minutes after first contact of sponge to chitosan layer. Once all lyophilizer shelves are loaded and the door secured, wait at least 20 minutes to allow the sample loaded last to reach freezing temperature. Stop the manual shelf freezing and begin a 12 hour lyophilization cycle beginning at −35° C. as follows:

| FREEZING | | |
|---|---|---|
| TEMP | −35 | −35 |
| TIME | 0 | 30 |

| EXTRA FREEZE | |
|---|---|
| TEMP | −35 |
| TIME | 1 |
| PRESS | 200 |

| PRIMARY DRYING | | | | | | | | |
|---|---|---|---|---|---|---|---|---|
| TEMP | −35 | −20 | −20 | −15 | −15 | −5 | −5 | 25 | 25 |
| TIME | 30 | 30 | 30 | 30 | 30 | 30 | 60 | 150 | 300 |
| PRESS | 200 | 200 | 200 | 200 | 200 | 200 | 200 | 200 | 200 |

After 12 hours, remove samples from lyophilizer and record "post-mass" in a log. In the event that cutting and packaging cannot immediately follow this step, store lyophilized sheets on HDPE in a dry, protected container (up to 1 week) until needed. Defrost and clean lyophilizer.

Example 3

Preparation of a Self Adhesive Resorbable Collagen Matrix with a Chitosan Salt Adhesive Layer A 3.5 wt % chitosan chloride solution was prepared by adding 0.7 g of chitosan chloride salt, (FMC BioPolymer) in incremental quantities of 0.2 g to 20 ml of deionized (DI) water. The solution was stirred by hand after each incremental addition of chitosan chloride salt. Next, the solution was split equally into two beakers. A 5.5 wt % solution was then prepared by adding 0.2 grams of chitosan chloride salt to one beaker of the 3.5 wt % solution and stirring by hand. Both solutions were transparent and homogenous containing no visible solids. Three milliliters of each solution was then applied to a 3"×3" collagen sponge. Application was conducted by hand using a stainless steel spatula at a ratio of 0.33 ml per square inch. Each sample was left at room temperature for three minutes, and then frozen and lyophilized overnight to remove any excess water. The chitosan chloride left an off white/yellow solid on the treated side of the collagen sponge.

Additional matrix samples were prepared with chitosan glutamate (FMC BioPolymer) by utilizing the methodology described above. Samples were prepared with a 5 wt % salt solution and a 7 wt % salt solution.

A 3.5 wt % solution was prepared by adding 1.5 g chitosan chloride salt (FMC BioPolymer) to 50 ml DI water. A 5.5 wt % solution was prepared by adding 1 g chitosan chloride salt (FMC BioPolymer) to 18 ml of DI water. A 15 wt % solution was prepared by adding about 3.0 g chitosan chloride salt (FMC BioPolymer) to 20 ml of DI water. Each solution was drawn down by a draw-down bar (TMI Industries Bar No 300) on a plastic sheet and the backing of each collagen sponge was placed on the solution. The samples were left at room temperature for a period of time and were then frozen and lyophilized to remove any residual water.

Additional matrix samples were prepared utilizing other chitosan salts (CarboMer, Inc.). The samples were prepared as described immediately above. If solutions were not homogenous they were applied by hand rather than by draw-down bar. The salts utilized and their concentrations are presented in Table 2.

TABLE 2

| Salt | Concentration | How applied to collagen sponge | Time at room temperature |
|---|---|---|---|
| Chitosan glutamate | 5 wt % | Hand applied | 3 minutes |
| Chitosan glutamate | 7 wt % | Hand applied | 3 minutes |
| Chitosan lactate | 5 wt % | Draw down applied | 1 minute |
| Chitosan lactate | 8 wt % | Draw down applied | 1 minute |
| Chitosan malate | | Hand applied | 1 minute |
| Chitosan ascorbate | 5 wt % | Hand applied | 1 minute |
| Chitosan ascorbate pH 3.5 | 7 wt % | Hand applied | 1 minute |
| Chitosan ascorbate pH 1.5 | 7 wt % | Hand applied | 1 minute |
| Carboxymethyl chitosan | 6 wt % | Hand applied | 1 minute |

Example 4

Tension Adhesion Testing of a Self Adhesive Resorbable Collagen Matrix

To determine the ability of various self adherent matrices to adhere to tissue under aqueous conditions, a tension adhesion test was performed. The test was performed on matrix samples identified in the Table 3 below. Some matrix samples were sterilized prior to testing. Sterilization occurred by either electronic beam (e-beam) sterilization or ethylene oxide (EO) sterilization.

Initial set up for the adhesion test required preparing aluminum T bars to be used with an Instron machine (Model 5544). Loctite glue was uniformly applied to an aluminum T bar. Next, a matrix sample was placed untreated side up. The T bar was placed glue side down on the untreated side of the sample and held in place for 20 seconds using two 0.7 N weights. The weights were removed and the matrix sample was trimmed around the T bar. While trimming the matrix sample it was verified that the matrix sample was completely attached to the T bar. The T bar with the attached matrix was then set aside.

A second aluminum T bar was then prepared by uniformly applying Loctite glue to the bar. The T bar was then placed, glue side down, onto freshly thawed bovine pericardium (Spears Biologics) and held in place for 40 seconds with two 1.3 N weights. The weights were then removed and the pericardium was trimmed around the T bar. While trimming the pericardium it was verified that it was completely attached to the bar. The prepared T bar was then inserted into the top grip of the Instron machine.

Prior to inserting the previously prepared T bar with the attached matrix into the Instron machine, 1.0 ml of Phosphate buffer saline (PBS) was injected into the matrix. Within 50 seconds of applying the PBS to the matrix, the T bar was placed in the bottom Instron grip and the top and bottom grips were aligned to be parallel to one another and approximately 1 mm apart. An adhesion-test program was then run. The machine applied a preload of 0.7 N for 30 seconds to the matrix sample and the pericardium substrate, which was followed by a quasi static tensile loading to evaluate the peak adhesive force obtained between the matrix and the substrate. The matrix samples tested and their average tensile adhesive strength are shown in Table 3 which were considerably above the average tensile strength determined by the above protocol of a control collagen matrix that did not have an adhesive layer.

TABLE 3

| Sample | Average Tensile Adhesive Strength (N) |
|---|---|
| 5.5 wt % Chitosan Chloride (pre-sterile) | 0.99074 |
| 3.5 wt % Chitosan Chloride (pre-sterile) | 0.74203 |
| 7 wt % Chitosan Glutamate (pre-sterile) | 0.79 |
| 5 wt % Chitosan Glutamate (pre-sterile) | 1.42 |
| 5.5 wt % Chitosan Chloride (e-beam sterilized) | 1.04742 |
| 3.5 wt % Chitosan Chloride (e-beam sterilized) | 0.96424 |
| 7 wt % Chitosan Glutamate (e-beam sterilized) | 1.00 |
| 5 wt % Chitosan Glutamate (e-beam sterilized) | 1.22 |
| 5 wt % Chitosan Lactate (EO sterilized) | 0.54577 |
| 8 wt % Chitosan Lactate (EO sterilized) | 3.07484 |
| 3 wt % Chitosan Chloride (EO sterilized) | 0.50169 |
| 15 wt % Chitosan Chloride (EO sterilized) | 0.92587 |
| 5.5 wt % Chitosan Chloride (EO sterilized) | 0.60677 |
| 6 wt % Carboxymethyl Chitosan (EO sterilized) | 0.55489 |
| 7 wt % Chitosan Ascorbate pH 3.5 (EO sterilized) | 0.64474 |

TABLE 3-continued

| Sample | Average Tensile Adhesive Strength (N) |
| --- | --- |
| 7 wt % Chitosan Ascorbate pH 1.5 (EO sterilized) | 1.22051 |
| 5 wt % Chitosan Ascorbate pH 3.5 (EO sterilized) | 0.77322 |
| 10 wt % Chitosan Malate (EO sterilized) | 0.53632 |
| 5 wt % Chitosan Lactate (e-beam sterilized) | 1.00016 |
| 8 wt % Chitosan Lactate (e-beam sterilized) | 1.00759 |
| 3 wt % Chitosan Chloride (e-beam sterilized) | 1.88849 |
| 15 wt % Chitosan Chloride (e-beam sterilized) | 1.30108 |
| 5.5 wt % Chitosan Chloride (e-beam sterilized) | 1.02817 |
| 6 wt % Carboxymethyl Chitosan (e-beam sterilized) | 0.59525 |
| 7 wt % Chitosan Ascorbate pH 1.5 (e-beam sterilized) | 0.63881 |

Additional chitosan samples were tested for adhesion using a collagen matrix (DURAGEN XS) without adhesive as a control. The results are presented in Table 4 below.

TABLE 4

| TENSION ADHESION TESTING | sample | load (N) | avg load (N) |
| --- | --- | --- | --- |
| DuraGen XS | control | 0.23 | 0.23 |
|  | control | 0.22 |  |
| DuraGen XS | control | 0.62 | 0.43 |
|  | control | 0.24 |  |
| DuraGen XS | control | 0.41 | 0.36 |
|  | control | 0.31 |  |
| DT-92 (70:30 LMW chitosan:MMW chitosan) | 1 | 1.40 | 1.03 |
|  | 2 | 1.03 |  |
|  | 3 | 0.76 |  |
|  | 4 | 0.92 |  |
| DT-92 (30:70 LMW chitosan:MMW chitosan) | 21 | 1.98 | 1.70 |
|  | 22 | 1.45 |  |
|  | 23 | 1.78 |  |
|  | 24 | 1.60 |  |
| DT-93 (MMW chitosan) | 1 | 1.46 | 1.30 |
|  | 2 | 1.15 |  |
|  | 3 | 1.22 |  |
|  | 4 | 1.37 |  |
| DT-94 (18 wt % LMW chitosan) | 4 | 1.25 | 1.78 |
|  | 26 | 1.24 |  |
|  | 53 | 3.45 |  |
|  | 71 | 1.47 |  |
|  | 88 | 1.48 |  |
|  | 144 | 2.19 | 2.47 |
|  | 146 | 2.89 |  |
|  | 147 | 1.68 |  |
|  | 148 | 2.80 |  |
|  | 149 | 2.78 |  |
|  | 11 | 1.77 | 1.52 |
|  | 12 | 2.76 |  |
|  | 21 | 0.92 |  |
|  | 23 | 0.99 |  |
|  | 27 | 1.15 |  |
| DT-95 (70:30 LMW chitosan:MMW chitosan) | 4 | 2.87 | 2.18 |
|  | 11 | 1.47 |  |
|  | 24 | 1.99 |  |
|  | 29 | 2.64 |  |
|  | 42 | 1.94 |  |
|  | 64 | 2.31 | 3.30 |
|  | 66 | 2.97 |  |
|  | 67 | 3.27 |  |
|  | 68 | 4.15 |  |
|  | 69 | 3.81 |  |
| DT-97 (30:70 LMW chitosan:MMW chitosan) | 3 | 2.28 | 2.55 |
|  | 4 | 3.40 |  |
|  | 6 | 1.20 |  |
|  | 7 | 3.31 |  |
| DT-98 (MMW chitosan) | 4 | 3.96 | 3.28 |
|  | 5 | 2.96 |  |
|  | 6 | 2.43 |  |
|  | 7 | 3.77 |  |

Example 5

Vertical Slide Testing of a Self Adhesive Resorbable Collagen Matrix Capable of Adhering to Tissue Under Aqueous Conditions To further verify the ability of various chitosan salts to adhere to tissue under aqueous conditions, a vertical slide test was performed. The test was performed on matrix samples identified in Table 5 below. Initially, a 10"×12" anodized aluminum tray was placed on a hot plate to be heated to 37±3° C. The tray was marked at 5.5" and 6.5" from the 10" edge. A 1 L beaker was then inverted and placed in a large containment tray and a 5 L carboy was placed on a 12" stool. Tygon tubing was run from the pour spout of the carboy and attached to the beaker. The tubing outlet was positioned downward at a 45° angle exactly 6.5" above the table surface.

Sample preparation was begun by cutting homogenized collagen sausage casing (Nippi) into 2" wide strips and adhering it to the preheated aluminum tray using water surface tension. The sausage casing strip was wet with 0.25 ml DI water. A matrix sample was then placed salt treated side down on the strip. A 62 g non-metallic mass was gently placed on the sample for 10 seconds. After the weight was removed, 0.75 ml DI water was directly applied to the sample. The tray with the sample attached was then placed in a vertical position and the hose outlet was placed so it gently abutted the sample. The temperature of the sausage casing was taken to verify it was 37±3° C. Next, the sample was irrigated with water from the carboy. The irrigation occurred at a flow rate of 30 to 40 ml/sec. The time it took for the sample to fall from the tray or for 5.5 L to have irrigated was recorded. The matrix samples tested and their average irrigation time are displayed in Table 5.

TABLE 5

| Sample | Average Duration (sec) |
| --- | --- |
| 5.5 wt % Chitosan Chloride (pre sterile) | 69.63 |
| 3.5 wt % Chitosan Chloride (pre sterile) | 106.62 |
| 7 wt % Chitosan Glutamate (pre sterile) | 143.15 |
| 5 wt % Chitosan Glutamate (pre sterile) | 160.04 |

Additional chitosan samples were tested for vertical slide using a collagen matrix (DURAGEN XS) without adhesive as a control. The results are presented in Table 5 below.

TABLE 5

| VERTICAL SLIDE TESTING | sample | time (sec) | avg time (sec) |
| --- | --- | --- | --- |
| DuraGen XS | Control | 0.49 | N/A |
| Duragen XS | Control | 0.51 | 0.51 |
| DuraGen XS | Control | 0.36 | 0.36 |
| DT-92 (70:30 LMW chitosan:MMW chitosan) | 1 | 85.62 | 55.39 |
|  | 2 | 32.01 |  |
|  | 3 | 64.92 |  |
|  | 4 | 39.02 |  |
| DT-92 (30:70 LMW chitosan:MMW chitosan) | 21 | 184.78 | 156.62 |
|  | 22 | 165.89 |  |
|  | 23 | 177.93 |  |
|  | 24 | 97.88 |  |
| DT-93 (MMW chitosan) | 1 | 161.39 | 133.46 |
|  | 2 | 89.72 |  |
|  | 3 | 158.77 |  |
|  | 4 | 123.94 |  |
| DT-94 (18 wt % LMW chitosan) | 4 | 99.68 | 92.91 |
|  | 26 | 46.04 |  |
|  | 53 | 114.54 |  |

TABLE 5-continued

| VERTICAL SLIDE TESTING | sample | time (sec) | avg time (sec) |
|---|---|---|---|
| | 71 | 92.91 | |
| | 88 | 111.40 | |
| | 144 | 91.70 | 105.33 |
| | 146 | 86.63 | |
| | 147 | 204.47 | |
| | 148 | 68.34 | |
| | 149 | 75.53 | |
| | 11 | 86.88 | 71.84 |
| | 12 | 108.35 | |
| | 21 | 39.90 | |
| | 23 | 62.83 | |
| | 27 | 61.24 | |

Example 6

In Situ Testing of a Self Adhesive Resorbable Matrix Capable of Adhering to Tissue Under Aqueous Conditions To quantitatively assess the adhesive bonding of a matrix in an environment similar to that encountered during surgery, a porcine model was utilized. The test was performed on various matrix samples. Initially, a porcine cranium was opened and the brain surface exposed to confirm the dura matter was intact. Once the dura was exposed, a dry 2×2 cm matrix sample was placed on an untested area of the dura that had been wet with PBS. The sample was placed in a vertical position and held in place for 10 seconds using a flat press. Alternatively, a sample was placed in a horizontal position and held in place for 10 seconds using fingertips. The sample was then wet out prior to irrigation. Next, the sample was irrigated with increasing force until it migrated. If the sample did not migrate a peel test was performed to assess the adherence of the sample to the dura. For some samples, additional tests were performed to assess the ability of the matrix samples to reattach to the dura after being removed, as well as their ability to attach to an area of the dura that had previously been treated.

The matrix samples tested include: chitosan chloride e-beam sterilized; chitosan chloride EO sterilized; chitosan chloride pre-sterilization; chitosan glutamate e-beam sterilized; chitosan lactate e-beam sterilized; chitosan lactate EO sterilized; chitosan ascorbate e-beam sterilized; chitosan ascorbate EO sterilized; chitosan acetate pre-sterilization; and carboxymethyl chitosan e-beam sterilized. Chitosan salts provided adequate resistance to migration in a porcine cranium evaluation and significantly greater than the DURAGEN matrix product without adhesive.

Alternatively, a matrix sample was placed on an untested area of dura that had been wet with PBS. The sample was placed in a more extreme vertical position and held in place for 10 seconds using fingertips. The sample was then wet out and irrigated with increasing force. After irrigation a manual peel test was performed and the sample was repositioned and held in place for 30 seconds using fingertips. The sample was then irrigated again until migration occurred.

Another alternative was to place a matrix sample on an untested area of the dura that had been wet with PBS. The sample was placed in a more extreme vertical position and held in place for 10 seconds using fingertips. After attachment and prior to wetting out, it was attempted to manually slide the sample out of place. The sample was then wet out and a manual peel test was performed. The sample was then repositioned on new dura and irrigated until migration occurred.

A final test of sample adherence was to handle the matrix sample with moist/wet gloves prior to attaching the sample to the dura as described above in an extreme vertical position. The sample was then wet out and irrigated with increasing force until migration occurred. If the sample did not migrate a manual peel test was performed.

The experiments showed that the self adhesive resorbable matrix with chitosan chloride as the adhesive demonstrated consistently excellent resistance to migration when applied to dry to moist dura and wet out prior to irrigation.

Example 7

In Situ Testing of a Self Adhesive Resorbable Matrix Capable of Adhering to Tissue Under Aqueous Conditions In addition, the following experiments were carried out using the porcine cranium model described above. The porcine model was utilized to obtain a semi-quantitative assessment of the functional performance of matrices having various adhesive layers of deacetylated chitosan (CHN) purchased from Adjuvant Pharmaceuticals, Alpharetta, Ga. Chitosan chloride salts were purchased from FMC BioPolymer, Ewing, N.J. The chitosan tested had a degree of deacetylation of between 50% to 80%, a molecular weight between about 50 kDa and 1000 kDa and a salt content of between 3% to 99%. The adhesive ability of the sample was graded on a scale of 1 to 10 with 1 being the lowest adhesive capability and 10 being the highest adhesive capability. Generally, a 10 was assigned for resistance to 5 consecutive irrigations without any sign of lost adhesive properties upon peeling the sample loose from the dura. The middle numbers in the scale were a linear range between the two extremes, for samples that resisted 1, 2, 3, or 4 irrigations but displayed some degree of decreased adhesive force. A control lacking an adhesive layer resulted in a "0 out of 10." The results are presented below.

An approximately three month old sample of 5.5 wt % chitosan chloride (FMC), 0.3 mm adhesive thickness, EO (DT-67-107) was placed on moist dura, which had been moistened with PBS. Sample was held in place for 10 seconds using a single finger; the sample was wet out prior to irrigation. The sample was irrigated five times. The sample provided significant resistance to peel when lifted with forceps and was evaluated as a "10 out of 10."

A sample of 5.5 wt % chitosan chloride (FMC), 0.3 mm adhesive thickness, EO (DT-67-107) was placed on moist dura, which had been moistened with PBS. Sample was held in place for 10 seconds using a single finger; the sample was wet out prior to irrigation. The sample did not migrate after 5 irrigations, and there was significant pull on the dura when the sample was peeled loose from the dura and was evaluated as a "10 out of 10".

A sample of 18 wt % LMW chitosan, 0.3 mm adhesive thickness, EO (DT-76-70) was placed on moist dura, which had been moistened with PBS. Sample was held in place for 10 seconds using a single finger; the sample was wet out prior to irrigation. The sample did not migrate after 5 irrigations, and there was significant pull on the dura when the sample was peeled loose from the dura and was evaluated as a "10 out of 10".

A sample of 6.5 wt % MMW chitosan, 0.3 mm adhesive thickness, EO (DT-89-1) was placed on moist dura, which had been moistened with PBS. Sample was held in place for 10 seconds using a single finger; the sample was wet out prior to irrigation. The top corner of the sample lifted after 4 irrigations but did not migrate after 5 irrigations. There was minimal pull on the dura when the sample was peeled loose and was evaluated as a "7 out of 10".

A sample of 6.5 wt % HMW chitosan, 0.3 mm adhesive thickness, EO (DT-76-33) was placed on moist dura, which had been moistened with PBS. Sample was held in place for 10 seconds using a single finger; the sample was wet out prior to irrigation. The sample edge of the sample lifted after the first irrigation, and migrated after the second irrigations and was evaluated as a "2 out of 10".

A sample of 80:20 LMW:HMW chitosan, 0.3 mm adhesive thickness, EO (DT-83-2) was placed on moist dura, which had been moistened with PBS. Sample was held in place for 10 seconds using a single finger; the sample was wet out prior to irrigation. The sample did not migrate after 5 irrigations. A peel test demonstrated significant pull against the dura and was evaluated as a "8 out of 10".

A sample of 6 wt % chitosan chloride (FMC) with an edge defect, 0.3 mm adhesive thickness, EO (DT-67-107) was placed on moist dura, which had been moistened with PBS. Sample was held in place for 10 seconds using a single finger; the sample was wet out prior to irrigation. Irrigation was purposely applied directly at the site of the defect, yet the sample did not migrate after 5 irrigations and was evaluated as a "10 out of 10".

A sample of 16 wt % water soluble chitosan (FMC), 0.3 mm adhesive thickness, Ebeam (DT-86-6) was placed on moist dura, which had been moistened with PBS. Sample was held in place for 10 seconds using a single finger; the sample was wet out prior to irrigation. The sample migrated after 2 irrigations and was evaluated as a "5 out of 10."

A sample of 60:40 LMW:HMW chitosan, 0.3 mm adhesive thickness, EO (DT-83-24) was placed on moist dura, which had been moistened with PBS. Sample was held in place for 10 seconds using a single finger; the sample was wet out prior to irrigation. The corner of the sample came up after 3 irrigations, and the sample did not migrate after 5 irrigations and was evaluated as a "7 out of 10".

A sample of 6.5 wt % MMW chitosan, 0.3 mm adhesive thickness, EO (DT-89-20) was placed on moist dura, which had been moistened with PBS. Sample was held in place for 10 seconds using a single finger; the sample was wet out prior to irrigation. The sample migrated after 2 irrigations and was evaluated as a "2 out of 10".

A sample of 6.5 wt % MMW chitosan, 0.3 mm adhesive thickness, EO (DT-89-1) was placed on moist dura, which had been moistened with PBS. Sample was held in place for 10 seconds using a single finger; the sample was wet out prior to irrigation. The corner of the sample lifted after 1 irrigation, the majority of the sample lifted after 2 irrigations, and the sample migrated after 4 irrigations and was evaluated as a "3 out of 10".

The following additional experiments were conducted:

An approximately five month old sample of 5.5 wt % chitosan chloride (FMC) (DT-54-49) was placed on moist dura, which had been moistened with PBS. Sample was held in place for 10 seconds using a single finger; the sample was wet out prior to irrigation. The sample was irrigated five times. The sample provided significant resistance to peel when lifted with forceps and was evaluated as a "10 out of 10."

An approximately five month old sample of 5.5 wt % chitosan chloride (FMC) (DT-55-19), which had been moistened with PBS. Sample was held in place for 10 seconds using a single finger; the sample was wet out prior to irrigation. The sample was irrigated five times. The sample provided significant resistance to peel when lifted with forceps and was evaluated as a "10 out of 10."

An approximately five month old sample of 18 wt % LMW chitosan (DT-71-13) was placed on moist dura, which had been moistened with PBS. Sample was held in place for 10 seconds using a single finger; the sample was wet out prior to irrigation. The edge of the sample lifted after the second irrigation. The sample provided moderate resistance to peel when lifted with forceps and was evaluated as a "8 out of 10".

A sample of 18 wt % LMW chitosan (DT-71-31) was placed on moist dura, which had been moistened with PBS. Sample was held in place for 10 seconds using a single finger; the sample was wet out prior to irrigation. The sample was irrigated five times. The sample provided significant resistance to peel when lifted with forceps and was evaluated as a "10 out of 10".

A sample of 18 wt % LMW chitosan (DT-71-32) was placed on moist dura, which had been moistened with PBS. Sample was held in place for 10 seconds using a single finger; the sample was wet out prior to irrigation. The sample was irrigated five times. The sample provided significant resistance to peel when lifted with forceps and was evaluated as a "10 out of 10".

A sample of 18 wt % LMW chitosan (DT-76-74 (P-4)) was placed on moist dura, which had been moistened with PBS. Sample was held in place for 10 seconds using a single finger; the sample was wet out prior to irrigation. The sample was irrigated five times. Half of the sample lifted after the fourth irrigation. The sample provided some resistance to peel when lifted with forceps and was evaluated as a "9 out of 10".

A sample of 6.5 wt % MMW chitosan (DT-89-6) was placed on moist dura, which had been moistened with PBS. Sample was held in place for 10 seconds using a single finger; the sample was wet out prior to irrigation. The sample lifted at the corner after 1 irrigation and migrated upon second irrigation and was evaluated as a "3 out of 10".

A sample of 6.5 wt % MMW chitosan (DT-89-8) was placed on moist dura, which had been moistened with PBS. Sample was held in place for 10 seconds using a single finger; the sample was wet out prior to irrigation. The sample began to lift on the third irrigation. The sample migrated nearly completely after fifth irrigation. The sample provided a small resistance to peel when lifted the corner that remained stuck to the dura and was evaluated as a "7 out of 10".

A sample of (70:30) 18 wt % LMW chitosan: 6.5 wt % MMW chitosan (DT-92-5) was placed on moist dura, which had been moistened with PBS. Sample was held in place for 10 seconds using a single finger; the sample was wet out prior to irrigation. The sample nearly completely migrated after the second irrigation. The sample migrated completely after the third irrigation and was evaluated as a "3 out of 10".

A sample of (30:70) 18 wt % LMW chitosan: 6.5 wt % MMW chitosan (DT-92-26) was placed on moist dura, which had been moistened with PBS. Sample was held in place for 10 seconds using a single finger; the sample was wet out prior to irrigation. The sample migrated after 1 irrigation and was evaluated as a "1 out of 10".

A sample of 6.5 wt % MMW chitosan (DT-93-5) was placed on moist dura, which had been moistened with PBS. Sample was held in place for 10 seconds using a single finger; the sample was wet out prior to irrigation. The sample migrated after the first irrigation and was evaluated as a "1 out of 10".

A sample of 18 wt % LMW chitosan (DT-94-1) was placed on moist dura, which had been moistened with PBS. Sample was held in place for 10 seconds using a single finger; the sample was wet out prior to irrigation. The first irrigation lifted up the edge of the sample. The sample did not completely migrate after 5 irrigations, and there was a slight pull on the dura when the remaining corner of the sample was peeled loose from the dura and was evaluated as a "7 out of 10".

A sample of 18 wt % LMW chitosan (DT-94-2) was placed on moist dura, which had been moistened with PBS. Sample was held in place for 10 seconds using a single finger; the sample was wet out prior to irrigation. The sample lifted on the third irrigation and was half off after 5 irrigations. There was a slight pull on the dura when the sample was peeled loose from the dura and was evaluated as a "8 out of 10".

A sample of 18 wt % LMW chitosan (DT-94-3) was placed on moist dura, which had been moistened with PBS. Sample was held in place for 10 seconds using a single finger; the sample was wet out prior to irrigation. The sample did not migrate after five irrigations. There was a significant pull on the dura when the sample was peeled loose from the dura and was evaluated as a "10 out of 10".

A sample of thicker layered 18 wt % LMW chitosan (DT-94-141) was placed on moist dura, which had been moistened with PBS. Sample was held in place for 10 seconds using a single finger; the sample was wet out prior to irrigation. Half of the sample lifted after the second irrigation, but did not migrate after 5 irrigations. There was some pull on the dura when the sample was peeled loose from the dura and was evaluated as a "7 out of 10".

A sample of thicker layered 18 wt % LMW chitosan (DT-94-142) was placed on moist dura, which had been moistened with PBS. Sample was held in place for 10 seconds using a single finger; the sample was wet out prior to irrigation. The sample was placed close to the dural defect which yielded the sample getting wet out during the hold. The sample did not migrate after five irrigations. There was some pull on the dura when the sample was peeled loose and was evaluated as a "7 out of 10".

A sample of 18 wt % LMW chitosan (DT-94-143) was placed on moist dura, which had been moistened with PBS. Sample was held in place for 10 seconds using a single finger; the sample was wet out prior to irrigation. The sample's edge lifted after the fifth irrigation. There was some pull on the dura when the sample was peeled loose and was evaluated as a "9 out of 10".

A sample of thicker layered 18 wt % LMW chitosan (DT-94-142) was placed on moist dura, which had been moistened with PBS. Sample was held in place for 10 seconds using a single finger; the sample was wet out prior to irrigation. The sample's edge began to lift after the second irrigation, but did not migrate after five irrigations. There was some pull on the dura when the sample was peeled loose and was evaluated as a "9 out of 10".

A sample of (70:30) 18 wt % LMW chitosan: 6.5 wt % MMW chitosan (DT-95-1) was placed on moist dura, which had been moistened with PBS. Sample was held in place for 10 seconds using a single finger; the sample was wet out prior to irrigation. The sample did not migrate after five irrigations, but lifted at the edge on the fifth irrigation. There was some pull on the dura when the sample was peeled loose and was evaluated as a "10 out of 10".

A sample of thicker layered (70:30) 18 wt % LMW chitosan: 6.5 wt % MMW chitosan (DT-95-2) was placed on moist dura, which had been moistened with PBS. Sample was held in place for 10 seconds using a single finger; the sample was wet out prior to irrigation. The sample did not migrate after five irrigations, but lifted at the edge on the fourth irrigation. The sample provided minimal resistance to peel when lifted off of the dura and was evaluated as a "8 out of 10".

A sample of (70:30) 18 wt % LMW chitosan: 6.5 wt % MMW chitosan (DT-95-3) was placed on moist dura, which had been moistened with PBS. Sample was held in place for 10 seconds using a single finger; the sample was wet out prior to irrigation. The sample did not migrate after five irrigations and had a very significant pull on the dura during the peel up. Irrigations did not appear to lift the sample at all and was evaluated as a "10 out of 10".

A sample of thicker layered (70:30) 18 wt % LMW chitosan: 6.5 wt % MMW chitosan (DT-95-61) was placed on moist dura, which had been moistened with PBS. Sample was held in place for 10 seconds using a single finger; the sample was wet out prior to irrigation. The sample did not migrate after 5 irrigations, but began to lift on the third irrigation. A peel test demonstrated some pull against the dura and was evaluated as a "8 out of 10".

A sample of thicker layered (70:30) 18 wt % LMW chitosan: 6.5 wt % MMW chitosan (DT-95-62) was placed on moist dura, which had been moistened with PBS. Sample was held in place for 10 seconds using a single finger; the sample was wet out prior to irrigation. The sample began to migrate after the second irrigation, but did not completely migrate after five irrigations. A peel test demonstrated some pull on the dura and was evaluated as a "7 out of 10".

A sample of thicker layered (70:30) 18 wt % LMW chitosan: 6.5 wt % MMW chitosan (DT-95-63) was placed on moist dura, which had been moistened with PBS. Sample was held in place for 10 seconds using a single finger; the sample was wet out prior to irrigation. The sample's corner lifted on the first irrigation, but did not completely migrate after five irrigations. A peel test demonstrated some pull on the dura and was evaluated as a "7 out of 10".

A sample of thicker layered 18 wt % LMW chitosan (DT-96-1) was placed on moist dura, which had been moistened with PBS. Sample was held in place for 10 seconds using a single finger; the sample was wet out prior to irrigation. The edge of the sample was lifted during the fourth irrigation, but did not migrate after five irrigations. A peel test demonstrated a slight pull on the dura and was evaluated as a "8 out of 10".

A sample of (30:70) 18 wt % LMW chitosan: 6.5 wt % MMW chitosan (DT-97-1) was placed on moist dura, which had been moistened with PBS. Sample was held in place for 10 seconds using a single finger; the sample was wet out prior to irrigation. The sample edge lifted after the first irrigation but did not migrate after five irrigations. A peel test demonstrated some pull on the dura and was evaluated as a "7 out of 10".

A sample of (30:70) 18 wt % LMW chitosan: 6.5 wt % MMW chitosan (DT-97-2) was placed on moist dura, which had been moistened with PBS. Sample was held in place for 10 seconds using a single finger; the sample was wet out prior to irrigation. The sample's top edge lifted after the second irrigation and migrated completely after four irrigations and was evaluated as a "6 out of 10".

A sample 6.5 wt % MMW chitosan (DT-98-1) was placed on moist dura, which had been moistened with PBS. Sample was held in place for 10 seconds using a single finger; the sample was wet out prior to irrigation. The sample was placed close to the dural defect which yielded the sample getting wet out during the hold. The sample migrated during the second irrigation and was evaluated as a "3 out of 10".

A sample of 6.5 wt % MMW chitosan (DT-98-2) was placed on moist dura, which had been moistened with PBS. Sample was held in place for 10 seconds using a single finger; the sample was wet out prior to irrigation. The sample began to migrate at the corner after the second irrigation and completely migrated on the fifth irrigation and was evaluated as a "7 out of 10".

A sample of 6.5 wt % MMW chitosan (DT-98-1) was placed on moist dura, which had been moistened with PBS. The sample began to lift after the fourth irrigation but did not completely migrate after the five irrigations. A peel test demonstrated slight pull on the dura and was evaluated as a "8 out of 10".

A sample of 6.5 wt % MMW chitosan (DT-98-3) was placed on moist dura, which had been moistened with PBS. Sample was held in place for 10 seconds using a single finger; the sample was wet out prior to irrigation. The sample edge lifted after the first irrigation, and completely migrated after the third irrigation and was evaluated as a "5 out of 10".

Given the benefit of the above disclosure and description of exemplary embodiments, it will be apparent to those skilled in the art that numerous alternative and different embodiments are possible in keeping with the general principles of the invention disclosed here. Those skilled in this art will recognize that all such various modifications and alternative embodiments are within the true scope and spirit of the invention. The appended claims are intended to cover all such modifications and alternative embodiments. It should be understood that the use of a singular indefinite or definite article (e.g., "a," "an," "the," etc.) in this disclosure and in the following claims follows the traditional approach in patents of meaning "at least one" unless in a particular instance it is clear from context that the term is intended in that particular instance to mean specifically one and only one. Likewise, the term "comprising" is open ended, not excluding additional items, features, components, etc.

What is claimed is:

1. An adherent resorbable porous device for regenerating tissue in a patient, comprising:
    a biocompatible and resorbable collagen matrix sheet having pores of sizes that permit growing tissue to infiltrate therein; and
    an adhesive layer having a thickness from 0.10 mm to 1 mm of a dried adhesive on only one surface of the collagen matrix sheet, which when contacted with aqueous fluid provides adherence to a surface of the tissue and allows infiltration of cells of the tissue into the collagen matrix sheet, wherein the adhesive is selected from the group consisting of hydroxypropyl methyl cellulose, hydroxyethyl cellulose, and combinations thereof;
    wherein the adherent resorbable porous device has a porous structure that facilitates ingrowth of cells into the collagen matrix.

2. The adherent resorbable porous device of claim 1 further including a bioactive agent.

3. The adherent resorbable porous device of claim 1, wherein the hydroxypropyl methyl cellulose or hydroxyethyl cellulose has a molecular weight between 5 kDa and 2000 kDa.

4. The adherent resorbable porous device of claim 1, wherein a dye coloring agent is included in the adhesive layer or the collagen matrix sheet or both.

5. The adherent resorbable porous device of claim 1, wherein the matrix sheet has a thickness from 0.1 mm to 50 mm.

6. The adherent resorbable porous device of claim 1, wherein the matrix sheet includes pores of sizes from 1 µm to 1000 µm.

7. The adherent resorbable porous device of claim 1, wherein the matrix sheet includes pores of sizes from 10 µm to 500 µm.

8. The adherent resorbable porous device of claim 1, wherein the adhesive layer has a thickness from about 0.2 mm to about 0.5 mm.

9. The adherent resorbable porous device of claim 1, which is prepared by applying a solution of the adhesive onto the surface of a collagen matrix sheet, and then lyophilizing the collagen matrix sheet having the adhesive applied thereon.

10. The adherent resorbable porous device of claim 1, wherein the adhesive layer provides adherence to the surface of the tissue with an increased uniaxial adhesion from about 0.4N to about 10 N as determined by ASTM F-2258-05.

11. A method for preventing migration of a biocompatible and resorbable matrix during surgery of tissue in a patient, comprising:
    providing an adherent resorbable porous device comprising: a biocompatible and resorbable collagen matrix sheet having pores of sizes that permit growing tissue to infiltrate therein; and an adhesive layer having a thickness between 0.10 mm to 1 mm of a dried adhesive on only one surface of the collagen matrix sheet, which when contacted with aqueous fluid provides adherence to a surface of the tissue and allows infiltration of cells of the tissue into the collagen matrix sheet; wherein the adhesive is selected from the group consisting of hydroxypropyl methyl cellulose, hydroxyethyl cellulose, and combinations thereof; wherein the adherent resorbable porous device has a porous structure that facilitates ingrowth of cells into the collagen matrix;
    placing the adherent resorbable porous device over the tissue of the patient;
    allowing the adherent resorbable porous device to contact with aqueous fluid present on the tissue;
    allowing the biocompatible and resorbable collagen matrix to adhere to the tissue; and
    optionally securing the biocompatible and resorbable matrix to the site of tissue repair.

12. The method of claim 11 wherein the matrix sheet includes pores of sizes from 1 µm to 1000 µm.

13. The method of claim 11 wherein the matrix sheet includes pores of sizes from 1 µm to 1000 µm.

14. The method of claim 11, wherein the adhesive layer has a thickness from about 0.2 mm to about 0.5 mm.

15. The method of claim 11, wherein the adhesive layer provides adherence to the surface of the tissue with an increased uniaxial adhesion from about 0.4N to about 10 N as determined by ASTM F-2258-05.

16. A method of making a biocompatible and resorbable matrix comprising:
    providing a biocompatible and resorbable collagen matrix sheet having pores of sizes that permit growing tissue to infiltrate therein;
    applying a solution of adhesive to only one surface of the biocompatible and resorbable matrix, wherein the adhesive is selected from the group consisting of hydroxypropyl methyl cellulose, hydroxyethyl cellulose, and combinations thereof; and lyophilizing the collagen matrix sheet having the adhesive applied thereon, whereby an adhesive layer having a thickness 0.10 mm to 1 mm of dried hydroxypropyl methyl cellulose or hydroxyethyl cellulose adhesive is formed on the surface of the collagen matrix sheet, which when contacted with aqueous fluid provides adherence to a surface of the tissue and allows infiltration of cells of the tissue into the collagen matrix sheet, and wherein the adherent resorbable porous device has a porous structure that facilitates ingrowth of cells into the collagen matrix.

17. The method of claim 16, wherein the matrix sheet includes pores of sizes from 1 µm to 1000 µm.

18. The method of claim 16, wherein the matrix sheet includes pores of sizes from 1 µm to 1000 µm.

19. The method of claim 16, wherein the adhesive layer has a thickness from about 0.2 mm to about 0.5 mm.

20. The method of claim 16, wherein the adhesive layer provides adherence to the surface of the tissue with an increased uniaxial adhesion from about 0.4N to about 10 N as determined by ASTM F-2258-05.

* * * * *